US011242314B2

(12) United States Patent
Zhou et al.

(10) Patent No.: US 11,242,314 B2
(45) Date of Patent: Feb. 8, 2022

(54) SYNTHESIZING PET TRACERS USING [F-18]SULFONYL FLUORIDE AS A SOURCE OF [F-18]FLUORIDE

(71) Applicants: Dong Zhou, St. Louis, MO (US); Wenhua Chu, St. Louis, MO (US)

(72) Inventors: Dong Zhou, St. Louis, MO (US); Wenhua Chu, St. Louis, MO (US)

(73) Assignee: Washington University, St. Louis, MO (US)

( * ) Notice: Subject to any disclaimer, the term of this patent is extended or adjusted under 35 U.S.C. 154(b) by 135 days.

(21) Appl. No.: 15/403,954

(22) Filed: Jan. 11, 2017

(65) Prior Publication Data

US 2017/0197912 A1 Jul. 13, 2017

Related U.S. Application Data

(60) Provisional application No. 62/277,222, filed on Jan. 11, 2016.

(51) Int. Cl.
| | | |
|---|---|---|
| *C07C 315/04* | (2006.01) |
| *C07D 213/52* | (2006.01) |
| *C07D 213/71* | (2006.01) |
| *C07H 3/02* | (2006.01) |
| *C07H 19/06* | (2006.01) |
| *C07D 233/91* | (2006.01) |
| *C07D 207/09* | (2006.01) |
| *C07C 247/04* | (2006.01) |
| *C07C 67/307* | (2006.01) |
| *C07C 45/63* | (2006.01) |
| *C07C 303/22* | (2006.01) |
| *C07J 1/00* | (2006.01) |
| *C07B 59/00* | (2006.01) |

(52) U.S. Cl.
CPC .......... *C07C 315/04* (2013.01); *C07B 59/001* (2013.01); *C07B 59/002* (2013.01); *C07B 59/005* (2013.01); *C07C 45/63* (2013.01); *C07C 67/307* (2013.01); *C07C 247/04* (2013.01); *C07C 303/22* (2013.01); *C07D 207/09* (2013.01); *C07D 213/52* (2013.01); *C07D 213/71* (2013.01); *C07D 233/91* (2013.01); *C07H 3/02* (2013.01); *C07H 19/06* (2013.01); *C07J 1/007* (2013.01); *C07B 2200/05* (2013.01)

(58) Field of Classification Search
None
See application file for complete search history.

(56) References Cited

U.S. PATENT DOCUMENTS

| 7,744,851 B2 | 6/2010 | DiMagno et al. | |
| 2011/0006011 A1* | 1/2011 | Aerts | A61K 51/04 |
| | | | 210/682 |
| 2012/0283490 A1* | 11/2012 | Gangadharmath | B01J 4/008 |
| | | | 570/153 |
| 2013/0005956 A1 | 1/2013 | Gangadharmath et al. | |
| 2014/0039074 A1 | 2/2014 | Chi et al. | |
| 2015/0232392 A1 | 8/2015 | Chi et al. | |

FOREIGN PATENT DOCUMENTS

| WO | 2011141410 A1 | 11/2011 |
| WO | 2015143019 A2 | 9/2015 |

OTHER PUBLICATIONS

Borders, C.L. et al., "Synthesis of Sulfonyl Fluorides by Use of a Fluoride Ion Exchange Resin" J. Org. Chem., 1972, pp. 3549-3550 (Year: 1972).*
Murakami, M., et al., "Novel preconcentration technique using bis(2-ethylhexyl) hydrogen phosphate (HDEHP) loaded porous polytetrafluoroethylene (PTFE) filter tube as a sorbent: Its application to determination of In(III) in seawater by ICP-MS with air segmented", Anal. Chim. Acta, 2006, pp. 423-429 (Year: 2006).*
Neal, T.R., et al., "Improved synthesis of 18F-fluoromethyl tosylate, a convenient reagent for radiofluoromethylations", J Label Comp. and Radiopharm., 2005, pp. 557-568 (Year: 2005).*
EMD Millapore, "Crown ethers and Kryptofix for professional applications", accessed from: https://pr.vwr.com/assetsvc/asset/en_US/id/17030245/contents, Oct. 2015, pp. 1-4 (Year: 2015).*
Fiel, S.A., "Pre-concentration of Positron-emitting [18F]Fluoride and Radiosynthesis of Fluoride-based Prosthetic compounds for PET imaging using magnetic droplet microfluidics (MDM)", Simon Fraser University, pp. 1-100, (Year: 2014).*
Wainerdi, R.E., et al., "Modern Methods of Geochemical Analysis", Springer, pp. 89 (Year: 1971).*
Aerts, J. et al., "Fast production of highly concentrated reactive [18F] fluoride for aliphatic and aromatic nucleophilic radiolabelling," Tetrahedron Lett., Jan. 6, 2010, pp. 64-66, vol. 51, No. 1, Elsevier Ltd.
Beyerlein, F. et al., "Automated synthesis and purification of [18F] fluoro-[di-deutero]methyl tosylate," J. Label. Compd. Radiopharm., Jun. 15, 2013, pp. 360-363, vol. 56, No. 7, John Wiley & Sons, Ltd.
Cai, L. et al., "Chemistry with [18F]Fluoride Ion," Eur. J. Org. Chem., Jun. 2008, pp. 2853-2873, vol. 2008, No. 17, Wiley-VCH Verlag GmbH & Co. KGaA, Weinheim.
Dong, J. et al., "Sulfur(VI) Fluoride Exchange (SuFEx): Another Good Reaction for Click Chemistry," Angew. Chem. Int. Edit., Sep. 1, 2014, pp. 9430-9448, vol. 53, No. 36, Wiley-VCH Verlag GmbH & Co. KGaA, Weinheim.
Fiel, S. et al., "Magnetic Droplet Microfluidics as a Platform for the Concentration of [18F]Fluoride and Radiosynthesis of Sulfonyl [18F]Fluoride," ACS Appl. Mater. Interfaces, 2015, pp. 12923-12929, vol. 7, No. 23, American Chemical Society.

(Continued)

Primary Examiner — Michael G. Hartley
Assistant Examiner — Lance W Rider
(74) Attorney, Agent, or Firm — Polsinelli PC

(57) ABSTRACT

The present disclosure relates to the methods for the preparation of reactive [F-18]fluoride in a form of [F-18]sulfonyl fluoride suitable for efficient radiolabeling without an azeotropic evaporation step by the use of anion exchange resin and sulfonyl chloride, and its applications in the manufacturing of PET radiopharmaceuticals.

18 Claims, 3 Drawing Sheets

(56) References Cited

OTHER PUBLICATIONS

Gatley, S., "Rapid Production and Trapping of [18F]fluorotrimethylsilane, and its use in nucleophilic fluorine-18 labeling without an aqueous evaporation step," Intnl. J. Radiation Appl. Instrumentation. Part A. Appl. Radiat. Isotopes, 1989, pp. 541-544, vol. 40, No. 6, Elsevier Ltd.

He, P. et al., "Advances in processes for PET radiotracer synthesis: Separation of [18F]fluoride from enriched [18O] water," Appl, Radiat. Isotopes, Sep. 2014, pp. 64-70, vol. 91, Elsevier Ltd.

Inkster, J. et al., "Sulfonyl Fluoride-Based Prosthetic Compounds as Potential 18F Labelling Agents," Chem. Eur. J., Aug. 27, 2012, pp. 11079-11087, vol. 18, No. 35, Wiley-VCH Verlag.

Inkster, J. et al., "Assessing the potential of sulfonyl fluorides as F-18-bearing prosthetic molecules," J. Labelled Compd. Radiopharma., 2011, pg. S75, vol. 54, Wiley-Blackwell, Malden, MA.

Jiang, H. et al., "Production and Transport of Gaseous 18F-Synthons: 18F-Acyl Fluorides," HHS Public Access Author Manuscript, available in PMC on Dec. 1, 2016, pp. 1-13, published in final edited form as: J. Fluor. Chem., Dec. 2015, pp. 181-185, vol. 180.

Lemaire, C. et al., "Fast Production of Highly Reactive No-Carrier-Added [18F]Fluoride for the Labeling of Radiopharmaceuticals," Angew. Chem. Int. Edit., Apr. 19, 2010, pp. 3161-3164, vol. 49, No. 18, Wiley-VCH Verlag.

Lindner, S. et al., "Azeotropic drying free [18F]FDG synthesis and its application to a lab-on-chip platform," Chem. Commun., 2016, pp. 729-732, vol. 52, The Royal Society of Chemistry.

Matesic, L. et al., "Ascertaining the Suitability of Aryl Sulfonyl Fluorides for [18F]Radiochemistry Applications: A Systematic Investigation using Microfluidics," J. Org. Chem., 2013, pp. 11262-11270, vol. 78, American Chemical Society.

Matesic, L. et al., "A systematic investigation into the F-18-radiolabelling and stability of sulfonyl fluorides using microfluidics," J. Labelled Compd. Radiopharma., 2013, p. S475, vol. 56, Wiley-Blackwell, Hoboken, NJ.

Mulholland, G., "Recovery and Purification of No-carrier-added [18F]Fluoride with Bistrimethylsilysulfate (BTMSS)," Appl. Radiat. Isot., 1991, pp. 1003-1008, vol. 42, No. 11, Pergamon Press plc.

Nielsen, M. et al., "A Low-Cost, Stable, and Selective Deoxyfluorination Reagent." J. Am. Chem. Soc., Jul. 15, 2015, pp. 9571-9574, vol. 137, American Chemical Society.

Ohsaki, K. et al., "Polymer-supported catalysts for efficient on-column preparation of 2-deoxy-2-[18F]fluoro-D-glucose," Appl. Radiat. Isotopes, Apr. 1998, pp. 373-378, vol. 49, No. 4, Elsevier Science Ltd., Great Britain.

Richarz, R. et al., "Neither azeotropic drying, nor base nor other additives: a minimalist approach to 18F-labeling," Org. Biomol. Chem., 2014, pp. 8094-8099, vol. 12, The Royal Society of Chemistry.

Seo, J. et al., "Fast and Easy Drying Method for the Preparation of Activated [18F]Fluoride Using Polymer Cartridge," Bull. Korean Chem. Soc., 2011, pp., 71-76, vol. 32, No. 1.

Sewing, C. et al. "A new nucleophilic radiofluorination reagent for fast and mild radiofluorination reaction," 21st International Symposium on Radiopharmaceutical Sciences, Oral Presentations, J. Label. Compd. Radiopharm., May 26-31, 2015, p. S2, vol. 58.

Tang, G. et al., "Fully automated synthesis module for preparation of S-(2-[18F]fluoroethyl)-L-methionine by direct nucleophilic exchange on a quaternary 4-aminopyridinium resin," Nucl. Med. Biol., May 2003, pp. 509-512, vol. 30, No. 5, Elsevier Inc.

Toorongian, S. et al., "Routine Production of 2-Deoxy-2-[18F]fluoro-D-Glucose by Direct Nucleophilic Exchange on a Quaternary 4-Aminopyridinium Resin," Nucl. Med. Biol., 1990, pp. 273-279, vol. 17, No. 3, Pergamon Press plc, Great Britain.

\* cited by examiner a) one pass b) back & forth c) circulating

SYNTHESIZING PET TRACERS USING [F-18]SULFONYL FLUORIDE AS A SOURCE OF [F-18]FLUORIDE

CROSS REFERENCE TO RELATED APPLICATIONS

This application claims the benefit of U.S. Provisional Application No. 62/277,222, filed Jan. 11, 2016, the disclosure of which is hereby incorporated by reference in its entirety.

GOVERNMENTAL RIGHTS

This invention was made with government support under DESC0008432 awarded by the Department of Energy and CA025836 awarded by the National Institutes of Health. The government has certain rights in the invention.

FIELD OF THE INVENTION

The present disclosure relates to the methods for the preparation of reactive [F-18]fluoride in a form of [F-18]sulfonyl fluoride suitable for efficient radiolabeling without an azeotropic evaporation step by the use of anion exchange resin and sulfonyl chloride, and its applications in the manufacturing of PET radiopharmaceuticals.

BACKGROUND OF THE INVENTION

Position emission tomography (PET) is an imaging technique that is commonly used in clinical and research settings. This technique requires a PET radioisotope labeled compound as a probe. Fluorine-18 (F-18) is the most commonly used PET isotope due to its facile availability from a medical cyclotron and favorable decay characters. F-18 labeling is typically completed through a nucleophilic substitution of a good leaving group (e.g. TsO, MsO, TfO) by [F-18]fluoride. However, [F-18]fluoride is produced in O-18 water. The bulky water has to be removed in order to make fluoride reactive and the expensive O-18 water must then be recovered.

The conventional protocol for drying [F-18]fluoride for radiolabeling is: (1) Trap [F-18]fluoride in an anion exchange resin and recover O-18 water; (2) Elute [F-18] fluoride in an aqueous acetonitrile solution containing potassium carbonate or with Kryptofix K222 (K222); (3) Dry the mixture of [F-18]fluoride, potassium carbonate, and K222 at elevated temperatures by azeotropic evaporation under a flow of $N_2$, He, or Ar to generate "activated" or "naked" [F-18]fluoride that is sufficiently moisture-free for nucleophilic substitution.

Problems with the conventional method include: (1) The above steps are required for each individual radiosynthesis. It can take up to 30 min for the drying step, depending on the efficiency of drying. This is equivalent to up to 17.3% loss of radioactivity due to radiation decay; (2) Sufficient amount of water and potassium carbonate is needed to elute [F-18]fluoride efficiently from the cartridge. This may cause problems in drying and/or radiolabeling steps and the amount of potassium carbonate is less controllable for labeling; (3) The amount of water present after the above drying steps will vary from run to run, resulting in inconsistent radiolabeling. Too much water will not only reduce the reactivity of fluoride but also cause the decomposition of precursors much more quickly under the labeling condition. Over-drying will also hurt the labeling in various ways. A minimum of 10% fluoride will stick to glass reaction vessels even for properly dried fluoride with potassium carbonate/K222 and much more for over-dried fluoride. Up to 90% [F-18]fluoride may stick to the vessel when other bases (such as potassium bicarbonate) are used; (4) [F-18]fluoride processed by this method is contaminated with other ions (e.g. chloride, hydroxide.) eluted from the resin and heating during azetropical drying may decompose K222. All of these will result in low yields or even labeling failure. High reproducibility and reliability are critical for automated production of PET radiopharmaceuticals. In addition, the hardware requirement for azetropic drying limits the simplification of automated modules, the use of new technologies (such as microfluidics), and the storage of F-18 and on-demand synthesis of PET radiopharmaceuticals for patient use. The currently used method for drying [F-18] fluoride is a bottleneck for the production of F-18 radiopharmaceuticals.

Many methods have attempted to achieve the non-azeotropic drying of [F-18]fluoride, including (1) eluting trapped [F-18]fluoride in an anion exchange resin with an organic or an in organic base in organic solvents and (2) converting [F-18]fluoride chemically to a gaseous form (e.g. acetyl fluoride, triflate fluoride, and trimethylsilyl fluoride), which can be isolated from the reaction mixture and purified thereafter. However, various limitations inherited with these methods prevent their use in practice. Therefore, there is a need in the art to develop a fast and simple drying method to produce activated [F-18]fluoride.

SUMMARY OF THE INVENTION

In an aspect, the disclosure provides a method to extract out of an aqueous solution, concentrate and/or reformulate [F-18]fluoride without any evaporation step. The method comprises: (a) passing the aqueous [F-18]fluoride solution or solvent through a solid phase extraction column comprising an anion-exchange resin so that the [F-18]fluoride is trapped on the resin; (b) rinsing the resin with an organic solvent to eliminate the residual water; and (c) eluting the [F-18]fluoride with an eluting solution to release the [F-18] fluoride from the anion-exchange resin as [F-18]$RSO_2F$ which acts as a source of [F-18]fluoride for a labeling reaction, wherein the eluting solution comprises a compound having the formula $RSO_2R^1$ and an organic solvent, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof; and $R^1$ is a leaving group. In an embodiment, the method further comprises regenerating the [F-18]fluoride in the presence of at least one base and optionally at least one phase transfer catalyst during or before a labeling reaction.

In another aspect, the disclosure provides a method of making [F-18]sulfonyl fluoride. The method comprises: (a) passing an aqueous [F-18]fluoride solution through a solid phase extraction column comprising an anion-exchange resin so that the [F-18]fluoride is trapped on the resin; (b) rinsing the resin with an organic solvent to eliminate the residual water; and (c) eluting the [F-18]fluoride with an eluting solution to release the [F-18]fluoride from the anion-exchange resin as [F-18]$RSO_2F$ which acts as a source of [F-18]fluoride for a labeling reaction, wherein the eluting solution comprises a compound having the formula $RSO_2R^1$ and an organic solvent, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof; and $R^1$ is a leaving group. In an embodiment, the method further comprises regenerating the [F-18]fluoride in the presence of at least one base and optionally at least one phase transfer catalyst during or before a labeling reaction.

In still another aspect, the disclosure provides a method of using a compound comprising [F-18]$RSO_2F$ as a source of [F-18]fluoride for radiolabeling, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof.

In still yet another aspect, the disclosure provides a method of using of a compound comprising [F-18]$RSO_2F$ as a source of [F-18]fluoride for radiolabeling, wherein the compound comprising [F-18]$RSO_2F$ is used for synthesis of a PET radiotracer and wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof.

In a different aspect, the disclosure provides a method of synthesizing an F-18 labeled compound. The method comprises mixing [F-18]sulfonyl fluoride with at least one base and optionally at least one phase transfer catalyst and an aliphatic- or aromatic-precursor and heating the reaction mixture.

In another different aspect, the disclosure provides a method of synthesizing a PET radiotracer. The method comprises mixing [F-18]sulfonyl fluoride with at least one base and optionally at least one phase transfer catalyst and an aliphatic- or aromatic-precursor and heating the reaction mixture.

DETAILED DESCRIPTION OF THE INVENTION

Figure 1:
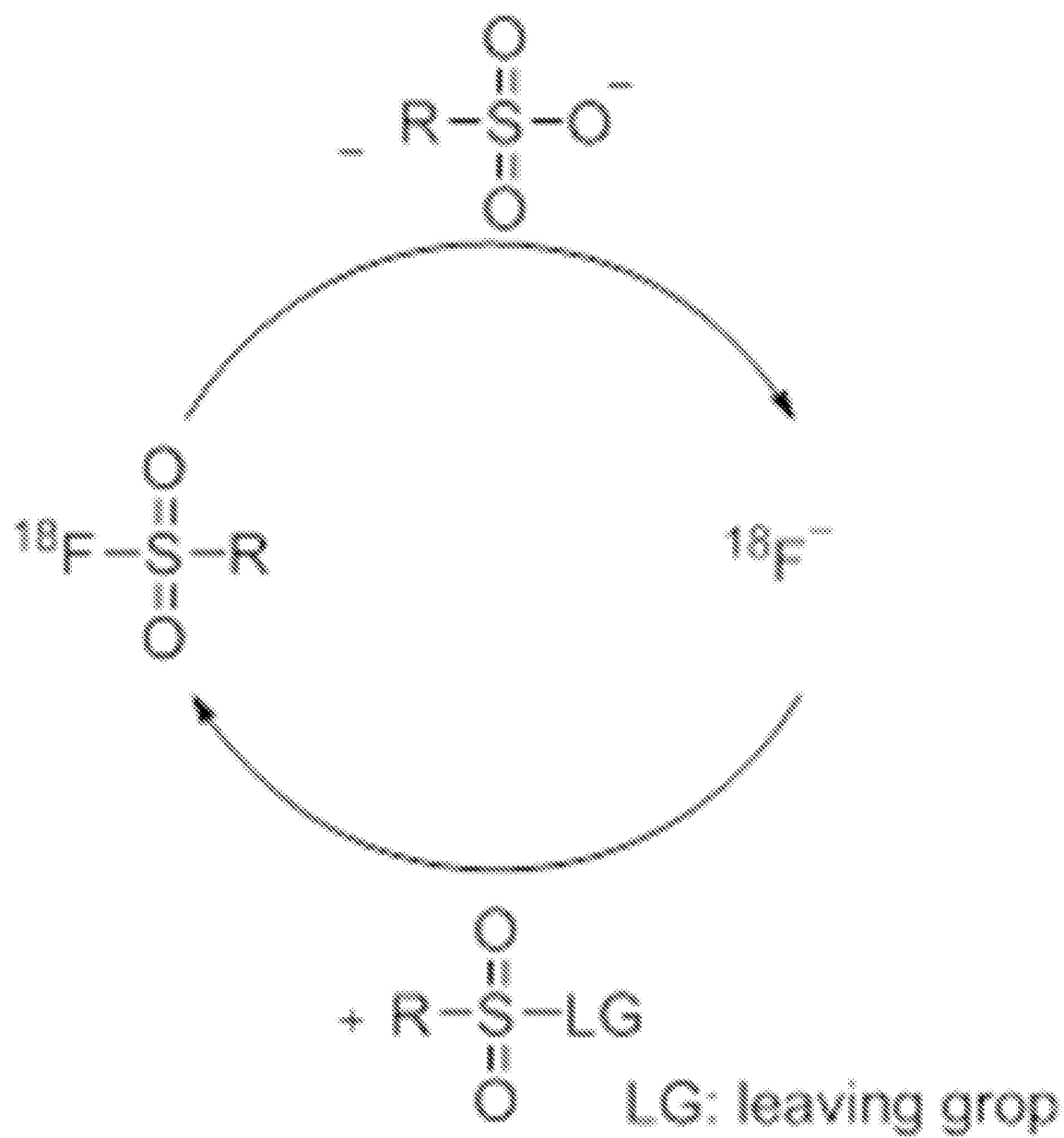
FIG. 1 depicts a schematic showing the generation of [$^{18}$F]sulfonyl fluoride and regeneration of [$^{18}$F]fluoride.

The disclosure provides use of a compound comprising [F-18]$RSO_2F$ as a source of [F-18]fluoride for radiolabeling. The disclosure also provides a method of producing [F-18]$RSO_2F$ comprising the use of a compound comprising $RSO_2R^1$ in an organic solvent as an eluting agent to release trapped [F-18]fluoride from a cartridge as a neutral molecule [F-18]$RSO_2F$, which acts as an [F-18]fluoride source for radiolabeling. Accordingly, no azeotropic drying is needed. In general, the procedure comprises: (a) Trap [F-18]fluoride in an anion exchange cartridge and recover O-18 water; (b) Rinse the cartridge with an organic solvent to remove residential water from the cartridge; and (c) Elute [F-18] from the cartridge as sulfonyl fluoride ($RSO_2F$) using a compound comprising $RSO_2R^1$ (e.g. 4-Toluenesulfonyl chloride or TsCl) in an organic solvent (acetonitrile, DMF, 2-amyl alcohol, ethanol, etc). During elution of F-18, the compound comprising $RSO_2R^1$ decomposes and is removed by the resin.

The [F-18]sulfonyl fluoride may then be used for radiolabeling, storage, or distribution of radioactivity to other sites for use. The labeling procedure may comprise: Method 1 (in situ). Mix [F-18]$RSO_2F$ in the eluting organic solvent with potassium carbonate/K222 (pre-dried as white solid) or other bases and a precursor. The mixture is then heated at the specified temperature; or Method 2 (pretreated). Mix [F-18]$RSO_2F$ in the eluting organic solvent with potassium carbonate/K222 (pre-dried as white solid) or other bases and heated briefly. The precursor in solution is added to this solution at the specified temperature and heated for the specified time.

The method of the present disclosure avoids the need for any azeotropic evaporation after the elution of the anion-exchange resin, reduces the duration of preparation which results in an increase in the overall radiochemical yield, simplifies the automated radiosynthesis equipment used for the synthesis of a radiotracer, is reliable and highly reproducible, and is suitable for implementation into automated systems. Ultimately, the method disclosed herein is simple, efficient, flexible, and high yielding in radiolabeling. This method is superior to automated production of radiopharmaceuticals. The use of this method in automated production will not only simplify the automated modules but also increase the reproducibility and reliability of production of radiopharmaceuticals. This method also facilitates the use of new technologies (e.g. microfluidics), on-demand-synthesis and distribution of radioactivity in the production of PET radiopharmaceuticals. This method also allows other applications such as determining specific activity of [F-18]fluoride by HPLC, and direct labeling of radiopharmaceutical with sulfonyl fluoride as a labeling tag.

Various aspects of the methods of the disclosure are described in more detail below.

I. Methods

In an aspect, the present disclosure encompasses the use of a compound comprising [F-18]$RSO_2F$ as a source of [F-18]fluoride for radiolabeling.

In another aspect, the present disclosure encompasses a method to extract out of an aqueous solution, concentrate and/or reformulate [F-18]fluoride without any azeotropic evaporation step. The method comprises: (a) passing the aqueous [F-18]fluoride solution or solvent through a solid phase extraction column comprising an anion-exchange resin so that the [F-18]fluoride is trapped on the resin; (b) rinsing the resin with an organic solvent to eliminate the residual water; and (c) eluting the [F-18]fluoride with an eluting solution to release the [F-18]fluoride from the anion-exchange resin as [F-18]$RSO_2F$ which acts as a source of [F-18]fluoride for a labeling reaction, wherein the eluting solution comprises a compound having the formula $RSO_2R^1$ and an organic solvent. In an embodiment, the method further comprises regenerating the [F-18]fluoride in the presence of at least one base during or before a labeling reaction. Optionally, the eluting solution further comprises a co-eluting agent.

In still another aspect, the disclosure provides a method of making [F-18]sulfonyl fluoride. The method comprises passing an aqueous [F-18]fluoride solution through a solid phase extraction column comprising an anion-exchange resin so that the [F-18]fluoride is trapped on the resin; rinsing the resin with an organic solvent to eliminate the residual water; and eluting the [F-18]fluoride with an eluting solution to release the [F-18]fluoride from the anion-exchange resin as [F-18]$RSO_2F$ which acts as a source of [F-18]fluoride for a labeling reaction, wherein the eluting solution comprises a compound having the formula $RSO_2R^1$ and an organic solvent. In an embodiment, the method further comprises regenerating the [F-18]fluoride in the presence of at least one base during or before a labeling reaction. Optionally, the eluting solution further comprises a co-eluting agent.

(a) F-18 Sulfonyl Fluoride

[F-18]$RSO_2F$ is used as a source of [F-18]fluoride for radiolabeling, storage, or distribution of radioactivity to other sites for use. As used herein, "sulfonyl fluoride" is a neutral molecule comprising the formula $RSO_2F$. Specifically, the sulfonyl fluoride is [F-18]$RSO_2F$. Sulfonyl fluoride is formed easily from the reaction of fluoride and a sulfonyl derivative comprising a leaving group ($RSO_2R^1$) under proper reaction conditions due to the high affinity of sulfur ($RSO_2$) to fluoride (see Table 1). The fluoride can be regenerated facilely and exclusively from sulfonyl fluoride by a base (OH—) in an organic solvent. Unlike fluoride which has high affinity for water and which in the form of $F—(H_2O)_n$ when azeotropically dried from aqueous solution, sulfonyl fluoride can be dried free of water and the fluoride regenerated from sulfonyl fluoride will have high reactivity towards nucleophilic reaction. Accordingly, [F-18]sulfonyl fluoride can be used as a vehicle to dry [F-18]fluoride with high reactivity (FIG. 1). Any suitable sulfonyl fluoride may be used in the methods of the disclosure.

Further, sulfonyl fluoride can be used to measure concentration of fluoride in water and in solvents. The formed [F-18]sulfonyl fluoride has high UV absorbance, which allows it to be detected by HPLC conveniently for quality control purposes or determining the specific activity of fluoride. The high UV absorbance which allows sulfonyl fluorides to be measured by UV as low as 0.1 ppm, which is equivalent to 0.01 ppm fluoride.

(b) Isolation of F-18 Sulfonyl Fluoride

[F-18]fluoride is produced by irradiation of enriched O-18 water. Only a minor fraction of the O-18 is converted. The F-18 isotope must be separated from the water and processed for production of a radiopharmaceutical agent. First the F-18 anions are separated from the enriched O-18 water and trapped on the anion-exchange resin. The F-18 loaded on the anion exchange resin is then prepared for elution. This preparation includes rinsing the cartridge with an organic solvent.

In general, the method to extract out of an aqueous solution, concentrate and/or reformulate [F-18]fluoride includes loading an amount of F-18 onto an anion exchange cartridge. About 0.05 mL to about 5 mL of the [F-18]fluoride in water is loaded onto an anion exchange cartridge. For example, about 0.05 mL to about 4 mL, about 0.05 mL to about 3 mL, about 0.05 mL to about 2 mL, about 0.05 mL to about 1 mL, about 0.05 mL to about 0.5 mL, about 0.1 mL, about 0.5 mL, or about 1 mL of the [F-18]fluoride in water is loaded onto an anion exchange cartridge. By anion exchange cartridge, what is meant is any vessel containing any convenient anion exchange resin or other material suitable for adsorbing [F-18]fluoride.

An anion-exchange resin or anion-exchange polymer is an insoluble matrix (or support structure) normally in the form of small beads or powder fabricated from an organic polymer substrate or inorganic silica gel. The trapping of anions occurs with the accompanying releasing of other anions; thus the process is called anion-exchange. There are multiple types of anion-exchange resin. Most typical anion-exchange resins are based on crosslinked polystyrene, others are based on silica gel and other functionalized polymeric sorbent (e.g. with N-vinylpyrrolidone). The counter ions are $CO_3^{2-}$, $HCO_3^-$, $OH^-$, $Cl^-$, and other anions or a combination of them. Anion resins may be either strongly or weakly basic. Strongly basic resins typically feature quaternary amino groups, for example, trialkylammonium groups (e.g. trimethylamine, triethylamine, tri-n-butyl amine, dimethyl-n-butylamine, N-methylimidazole, and pyridine) whereas weakly basic resins typically feature primary, secondary, and/or ternary amino groups (e.g. piperazine). Any suitable anion-exchange resin may be used in the method of the disclosure. Non-limiting examples of anion exchange resins include: Amberlite® Strong Anion Exchangers, Type I (Trialkylbenzyl Ammonium), Dowex® Type I (Trimethylbenzyl Ammonium), Amberlite®, Type II (Dimethyl-2-hydroxyethylbenzyl Ammonium), Dowex® Type II (Dimethyl-2-hydroxyethylbenzyl Ammonium), Amberlite® (Polyamine), Dowex® (Polyamine), or Duolite® (Polyamine) from Sigma-Aldrich; DIAION™ SA series (Gel Type), DIAION™ UBA120 (Gel Type), DIAION™ PA300 series (Porous Type), DIAION™ PA400 series (Porous Type), DIAION™ HPA25 (Highly Porous Type), DIAION™ WA10 (Acrylic Type), DIAION™ WA20 series (Polyamine Type), or DIAION™ WA30 (Dimethylamine Type) from Mitsubishi Chemical; UNOsphere™ Anion Exchange Resins, Macro-Prep® High Q Resin, Macro-Prep® DEAE Resin, or Macro-Prep® 25 Q Resin from Bio-Rad; and POROS® XQ resin from ThermoFischer.

The anion-exchange resin may be placed in a solid phase extraction column for use in the method of the disclosure. In an embodiment, the anion exchange resin comprises a polymeric matrix and quaternary ammonium groups. In some embodiments, the anion exchange resin is a strongly basic, macroporous resin comprising a styrene-divinylbenzene copolymer matrix and quaternary ammonium groups. In other embodiments, the anion exchange resin is a strongly basic, macroporous resin comprising a styrene-divinylbenzene copolymer matrix and quaternary and tertiary ammonium groups. Non-limiting examples of anion exchange cartridge/resins include: AG® MP-1 M and Bio-Rex™ 5 from Bio-Rad; Strata-X-A and SAX from Phenomenex; MAX and AccellPlus QMA from Waters; DSc-Sax and Ic-Sax from Supelco; Plexa PAX and SAX from Agilent; Chromafix PS-OH⁻ and Chromafix 30PS-HCO₃ from Macherey-Nagel; or a combination thereof. In a specific embodiment, the solid phase extraction column may be a Chromafix® cartridge. The counter ion may be $CO_3$, $HCO_3$, OH. In a specific embodiment, the solid phase extraction column is Chromafix 30PS-$HCO_3$. In another specific embodiment, the solid phase extraction column is AG® MP-1 M in bicarbonate form. In still another specific embodiment, the solid phase extraction column is Bio-Rex™ 5 in bicarbonate form.

After the loading of the [F-18]fluoride and prior to the elution step, the column is rinsed with an organic solvent at about 0° C. to about 100° C. that allows the elimination of the residual water that may be undesirable for a subsequent chemical processing, i.e. nucleophilic substitution, whilst keeping the extracted anions trapped on the resin. The column may be rinsed with an organic solvent at about 0° C. to about 25° C., about 0° C. to about 50° C., about 0° C. to about 80° C., about 25° C. to about 50° C., about 25° C. to about 80° C., about 25° C. to about 100° C., about 25° C., or about 80° C. The organic solvent is selected among solvents suitable for the subsequent radiolabeling reaction. The organic solvent is described in detail below. In a specific embodiment, the organic solvent is selected from the group consisting of acetonitrile (MeCN), dimethylformamide (DMF), 2-amyl alcohol, tetrahydrofuran (THF) and ethanol (EtOH). The column can be rinsed with about 1 mL to about 50 mL of the organic solvent. For example, the column may be rinsed with about 1 mL to about 40 mL, about 1 mL to about 30 mL, about 1 mL to about 20 mL, about 1 mL to about 10 mL, about 1 mL to about 5 mL, about 5 mL, or about 1 mL.

Next the F-18 is eluted from the cartridge by passing a solution at about 0° C. to about 100° C. comprising a compound having the formula $RSO_2R^1$ with or without a co-eluting agent and an organic solvent through the cartridge so as to obtain an F-18 solution containing [F-18]$RSO_2F$ and the organic solvent. The F-18 may be eluted at about 0° C. to about 25° C., about 0° C. to about 50° C., about 0° C. to about 80° C., about 25° C. to about 50° C., about 25° C. to about 80° C., about 25° C. to about 100° C., about 25° C., or about 80° C. The organic solvent is described in detail below. In a specific embodiment, the organic solvent is selected from the group consisting of acetonitrile (MeCN), dimethylformamide (DMF), 2-amyl alcohol, tetrahydrofuran (THF) and ethanol (EtOH). The F-18 can be eluted with about 0.1 mL to about 50 mL of the eluting solution. For example, the F-18 can be eluted with about 0.1 mL to about 40 mL, about 0.1 mL to about 30 mL, about 0.1 mL to about 20 mL, about 0.1 mL to about 10 mL, about 0.1 mL to about 5 mL, about 0.1 mL to about 1 mL, or about 0.5 mL.

F-18 is eluted from the anion exchange resin with an eluting solution comprising a compound having the formula $RSO_2R^1$, wherein R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof; and $R^1$ is a leaving group.

In certain embodiments, R is selected from the group consisting of alkyl, substituted alkyl, cycloalkyl, substituted cycloalkyl, aryl, substituted aryl, heteroaryl, substituted heteroaryl, methyl and trifluoromethyl. In other embodiments, R is selected from the group consisting of $CH_3$, $CF_3$, $C_6H_5$, $CH_3C_6H_4$, $CF_3C_6H_4$, $NO_2C_6H_4$, $ClC_6H_4$, $FC_6H_4$, $BrC_6H_4$, $IC_6H_4$, $CH_3COC_6H_4$, $MeOC_6H_4$, $CNC_6H_4$, $Me_2NC_6H_4$, 2,4,6-$(CH_3)_3C_6H_2$, and $C_5H_5N$ (pyridine).

A used herein a "leaving group" is a molecular fragment that departs with a pair of electrons in heterolytic bond cleavage. Leaving groups can be anions or neutral molecules and are a result of the formation of sulfonyl fluoride. Non-limiting examples of common anionic leaving groups are halides such as $Cl^-$, $Br^-$, and $I^-$. Additional leaving groups may include sulfonate ($RSO_2O^-$), azide ($N_3^-$), $^-CN$, acyl, alkoxide, $OH^-$, $NR^2_2$ (wherein $R^2$ is an alkyl), and N-phenyl-trifluoromethanesulfonimide (NTfPh). Non-limiting examples of sulfonates include tosylate (TsO), mesylate (MsO), trifluoromethanesulfate (triflate; TfO), nosylate (NsO), and besylate (BsO). In a specific embodiment, the leaving group is chloride. In another specific embodiment, the leaving group is selected from the group consisting of tosylate (TsO), mesylate (MsO), and trifluoromethanesulfate (triflate; TfO).

In an embodiment, $RSO_2$ is selected from the group consisting of tosyl (Ts), mesyl (Ms), trifluoromethanesulfonyl (Tf), nosyl (Ns), besyl (Bs) and NTfPh. In the foregoing embodiment, a polymer may be conjugated to $RSO_2$.

In an embodiment, the compound having the formula $RSO_2R^1$ is selected from the group consisting of tosyl chloride, mesyl chloride, trifluoromethanesulfonyl chloride, nosyl chloride, N-phenyl-bis(trifluoromethanesulfonimide), tosyl anhydride, mesyl anhydride, trifluoromethanesulfonic anhydride, tosyl mesylate, and tosyl triflate. In a specific embodiment, the compound having the formula $RSO_2R^1$ is tosyl chloride.

The amount of compound having the formula $RSO_2R^1$ added to the resin can and will vary based on the reaction reagents and conditions. The amount of compound having the formula $RSO_2R^1$ may be from about 0.1 mg to about 50 mg. For example, the amount of compound having the formula $RSO_2R^1$ may be from about 0.5 mg to about 40 mg, from about 1 mg to about 30 mg, from about 1 mg to about 20 mg, from about 1 mg to about 10 mg, or from about 1 mg to about 5 mg. Additionally, the amount of compound having the formula $RSO_2R^1$ may be about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, or about 5 mg. In a specific embodiment, the amount of compound having the formula $RSO_2R^1$ is about 1 mg.

As used herein, a "co-eluting agent" is any acid or its salt that will release trapped [F-18]fluoride from the anion exchange resin thereby facilitating elution with the eluting solution. Non-limiting examples of co-eluting agents include $TsOH/TsO^-$, $MsOH/MsO^-$, $TfOH/TfO^-$, $HCl/Cl^-$, $H_2SO_4^-/HSO_4^-/SO_4^{2-}$, and $AcOH/AcO^-$. In a specific embodiment, the co-eluting agent is TsOH (as $TsOH.H_2O$). The amount of co-eluting agent added to the eluting solution ranges from about 0.01 to about 1 equivalent of the compound having the formula $RSO_2R^1$. For example, the amount of co-eluting agent added to the eluting solution may range from about 0.01 to about 0.1, about 0.1 to about 1, about 0.05 to about 1, about 0.05 to about 0.5, about 0.05 to about 0.1, or about 0.1 to about 0.5 equivalent of the compound having the formula $RSO_2R^1$.

The elution solution also comprises an organic solvent. The solvent may be chosen without limitation from alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, amyl alcohol (including any of 8 alcohols with the formula $C_5H_{11}OH$), benzene, butyl acetate, chlorobenzene, chloroform, chloromethane, cyclohexane, cyclopentane, dichloromethane (DCM), dichloroethane, diethyl ether, dimethoxyethane (DME), dimethylacetamide (DMM), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. Additionally, primary alcohols such as methanol, ethanol, n-propanol, n-butanol, amyl alcohol, n-hexyl alcohol, n-heptanol, benzyl alcohol or n-octanol, secondary alcohols such as isopropanol, isobutanol, isoamyl alcohol or 3-pentanol, and tertiary alcohols, diols and polyols with 1 to 20 tertiary alcohol functions such as t-butanol, t-amyl alcohol, 2,3-dimethyl-2-butanol, 2-(trifluoromethyl)-2-propanol, 2,8-dimethyl-2,8-Decanediol, 2,5-dimethyl-3-Octyne-2,5-diol, or combinations thereof may be used. In a specific embodiment, the organic solvent is selected from the group consisting of acetonitrile, DMF, 2-amyl alcohol, THF, and ethanol.

Various elution methods known or new in the art can be used for eluting the [F-18]fluoride. Non-limiting examples include one-pass, back-and-forth, and circulating (see, for example, FIG. 3). The flow rate for elution ranges from about 0.1 mL/min to about 10 mL/min. For example, the flow rate for elution may range from about 0.1 mL/min to about 5 mL/min, about 0.1 mL/min to about 1 mL/min, about 0.1 mL/min to about 0.5 mL/min, about 0.5 mL/min to about 10 mL/min, about 0.5 mL/min to about 5 mL/min, about 0.5 mL/min to about 1 mL/min, about 1 mL/min to about 10 mL/min, about 1 mL/min to about 5 mL/min, or about 5 mL/min to about 10 mL/min. The elution process can be repeated from about 2 to about 100 times for the back-and-forth method. For example, the elution process may be repeated about 2 to about 75, about 2 to about 50, about 2 to about 25, about 2 to about 15, about 2 to about 10, about 5 to about 75, about 5 to about 50, about 5 to about 25, about 10 to about 75, about 10 to about 50, about 10 to about 25, about 25 to about 75, about 25 to about 50, about 50 to about 75, or about 75 to about 100 times for the back-and-forth method. Additionally, the elution process can be repeated from about 2 to about 100 cycles for the circulating method. For example, the elution process may be repeated about 2 to about 75, about 2 to about 50, about 2 to about 25, about 2 to about 15, about 2 to about 10, about 5 to about 75, about 5 to about 50, about 5 to about 25, about 10 to about 75, about 10 to about 50, about 10 to about 25, about 25 to about 75, about 25 to about 50, about 50 to about 75, or about 75 to about 100 cycles for the circulating method.

(c) Radiolabeling

The eluted organic solution containing the [F-18]$RSO_2F$ can then be used as a reagent for the synthesis of an F-18 labeled compound. Specifically, the [F-18]sulfonyl fluoride can be used for the synthesis of an F-18 labeled compound comprising sulfonyl fluoride as the labeled group via a conjugation reaction of the reagent. Alternatively, the eluted [F-18]$RSO_2F$ is a an F-18 labeled compound comprising sulfonyl fluoride as the labeled group. Non-limiting examples include sulfonyl fluoride derivatives of acids, aldehydes, N-hydroxysuccinimides, maleimides, alkynes, azides and pharmaceuticals containing sulfonyl fluoride as a functional group. Additionally, the eluted organic solution containing the [F-18]$RSO_2F$ can then be used for the synthesis of a PET radiotracer. Alternatively, the eluted [F-18]$RSO_2F$ is a PET radiotracer. [F-18]fluoride is regenerated during (in situ) or before the radiolabeling for substitution reactions on both aliphatic and aromatic precursors.

F-18-labeling is performed, without drying the [F-18] fluoride, in the presence of at least one base and, optionally, at least one phase transfer catalyst (PTC). Any suitable base may be used. Examples of bases include, but are not limited to, potassium carbonate ($K_2CO_3$), potassium bicarbonate ($KHCO_3$), cesium carbonate ($Cs_2CO_3$), cesium biocarbonate, potassium mesylate, potassium oxylate, and tetrabutylammonium and tetramethylammonium salts (hydroxide, carbonate, and bicarbonate). Non-limiting examples of suitable phase transfer catalysts include Kryptofix K222 and 18-crown-6. Specific combinations of base and phase transfer catalyst may include potassium carbonate/Kryptofix 222, potassium bicarbonate/Kryptofix 222, potassium carbonate/18-crown-6, and potassium bicarbonate/18-crown-6. In a specific embodiment, the combination of base and PTC is potassium carbonate and Kryptofix K222. These combinations may be pre-dried as a solid prior to use. The ratio of base to phase transfer catalyst may be from about 1:1 to about 1:5. For example, the ratio of base to phase transfer catalyst may be from about 1:1 to about 1:4, about 1:1 to about 1:3, about 1:1 to about 1:2. In a specific embodiment, the ratio of base to phase transfer catalysis is about 1:2.

The amount of base and optionally PTC may be about 0.1 to about 50 mg. For example, the amount of base and optionally PTC may be about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg or about 50 mg. In a specific embodiment, the about of base and PTC is about 5 mg. More specifically, the amount of $K_2CO_3/K_{222}$ (1:2) is about 5 mg.

In certain embodiments, the organic solvent suitable for the subsequent radiolabeling reaction is identical to the solvent used for elution. In one embodiment, the eluted [F-18]$RSO_2F$ in the eluting organic solvent is mixed with the at least one labeling reagent and at least one phase transfer catalyst and a precursor. The mixture is then heated to facilitate the reaction. Alternatively, the eluted [F-18]$RSO_2F$ in the eluting organic solvent is mixed with the at least one labeling reagent and at least one phase transfer catalyst and briefly heated. The precursor solution is then added to the mixture at a specified temperature and heated for a specified time. By "briefly heated" is meant that the mixture is heated to about 100-110° C. or about 105° C. for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 1 to about 5 minutes, about 2 to about 4 minutes, about 5 to about 10 minutes, about 10 to about 15 minutes, about 1 to about 15 minutes, about 5 to about 15 minutes, or about 1 to about 10 minutes.

The specified temperature may range from about 25° C. to about 250° C., including conventional heating, microwave heating and heating in microfluidics devices. For example, the temperature may range from about 60° C. to about 110° C., from about 65° C. to about 105° C., from about 70° C. to about 110° C., from about 80° C. to about 105° C., from about 80° C. to about 150° C., from about 80° C. to about 200° C., or from about 80° C. to about 250° C. Alternatively, the temperature may be about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 130° C., about 140° C., about 150° C., about 160° C., about 170° C., about 180° C., about 190° C., about 200° C., about 210° C., about 220° C., about 230° C., about 240° C., or about 250° C.

The reaction may proceed for about 5 minutes to about 30 minutes. For example, the reaction may proceed for about 7 minutes to about 20 minutes, about 7 minutes to about 15 minutes, or about 7 minutes to about 10 minutes. Alternatively, the reaction may proceed for about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, or about 30 minutes.

Examples of F-18-labeled PET probes that can be generated by the method of the present disclosure include, but are not limited to, [$^{18}$F]Fludeoxyglucose ("FDG"), [$^{18}$F]-3-Fluoro-2-(4-((2-nitro-1H-imidazol-1-yl)methyl)-1H-1,2,3-triazol-1-yl)propan-1-ol ("HX4" or "$^{18}$F-HX4"), fluorodeoxythymidine ("FLT"), 1-[$^{18}$F]fluoro-3-(2-nitro-1H-imidazol-1-yl)propan-2-ol ("F-MISO"), [$^{18}$F]-fluoroazomycinarabinofuranoside ("FAZA"), 5-[3-($^{18}$F)fluoropropyl]-2,3-dimethoxy-N-{[(2S)-1-(prop-2-en-1-yl)pyrrolidin-2-yl]methyl}benzamide ("Fallypride"), 9-(4-[$^{18}$F]Fluoro-3-hydroxymethylbutyl)guanine ("FHBG"), 9-[(3-[$^{18}$F]-fluoro-1-hydroxy-2-propoxy)methyl]guanine ("FHPG"), ($^{18}$F)fluoroethyl azide, $^{18}$F-4-fluorobenzaldehyde, $^{18}$F-4-fluoroethylbenzoate, $^{18}$F-4-fluoromethyl benzoate, and 7-Methoxy-2 (6-[$^{18}$F]fluoropyridin-3-yl)imidazo[2,1-b]-8-pyridinothiazole ("$^{18}$F-W372"). Other examples of F-18-labeled PET probes that can be generated by the method of the present disclosure include, but are not limited to, 2'-Deoxy-2'-[$^{18}$F]fluoro-5-fluoro-1-β-D-arabinofuranosyluracil ("FFAU"), as well as 1-[2-($^{18}$F)fluoroethyl]piperidin-3-yl hydroxy(diphenyl)acetate, 1-[2-($^{18}$F)fluoroethyl]piperidin-4-yl hydroxy(diphenyl)acetate, [$^{18}$F]FEDAA1106 N-(5-Fluoro-2-phenoxyphenyl)-N-(2-[18F]fluoroethyl-5-methoxybenzyl)acetamide, 1-(2-deoxy-2-fluoro-β-D-arabinofuranosyl)-5-[2-($^{18}$F)fluoroethyl]pyrimidine-2,4(1H,3H)-dione, [$^{18}$F]FECNT 2-Carbomethoxy-3-(4-chlorophenyl)-8-(2-[$^{18}$F]fluoroethyl)nortropane, [$^{18}$F]Fluoroethyl SA4503 1-(2-(4-[$^{18}$F]-fluoroethoxy-3-methoxyphenyl)ethyl)-4-(3-phenylpropyl)piperazine, 5-(2'-($^{18}$F)Fluoroethyl) flumazenil, N-(2-chloro-6-methylphenyl)-2-[(6-{4-[2-($^{18}$F)fluoroethyl]piperazin-1-yl}-2-methylpyrimidin-4-yl)amino]-1,3-thiazole-5-carboxamide, 3-[2-($^{18}$F)fluoroethyl]tyrosine, 3-[2-($^{18}$F)fluoroethyl]-O-methyltyrosine, [$^{18}$F]FDPN 6-O-(2-[$^{18}$F]fluoroethyl)-6-O-desmethyldiprenorphine, and [$^{18}$F]VM4-037 18F-(S)-3-(4-(2-fluoroethoxy) phenyl)-2-(3-methyl-2-(4-((2-sulfamoylbenzo[d]thiazol-6-yloxy)methyl)-1H-1,2,3-triazol-1-yl)butanamido) propanoic acid. Exemplary compounds are depicted in Table 5 below and include FDG, FLT, FMISO, fallypride, FES, FFNP, FNOS, fluoroethyltosylate, fluoroethylazide, WC-4-138, FC$_9$COOMe, 4-fluorobenzaldehyde and 4-fluorobenzoate ethyl ester.

A PET radiotracer synthesized via methods of the disclosure may be used in a PET scan. A PET scan uses a small amount of radioactive material (PET radiotracer). The radiotracer travels through blood and collects in organs and tissues facilitating their visualization. A PET scan may be used to check brain function, diagnose cancer, heart problems and brain disorders, determine metastasis of cancer, show areas in which there is poor blood flow to the heart, or determine if a tumor is malignant or benign. Several PET scans may be taken over time to check response to treatment for cancer or another illness.

Further, the methods disclosed herein can also be used to generate other F-18 labeled reagents by the same mechanism for F-18 labeling. Non-limiting examples include acyl fluoride and silyl fluoride.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group (CH$_2$=CH—CH$_2$—), but also to compounds that contain substituted allyl groups or allyl groups forming part of a ring system.

The term "alkyl" as used herein refers to straight or branched chain alkyl groups having in the range of about 1 to about 10 carbon atoms. A substituted alkyl group has one or more substituents as described in the definition of substituted hydrocarbyl. The term "lower alkyl" refers to straight or branched chain alkyl groups having in the range of about 1 to about 4 carbon atoms.

The term "alkylaryl" refers to alkyl substituted aryl groups, and "substituted alkylaryl" refers to alkylaryl groups further bearing one or more substituents.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl, or substituted naphthyl. The term "substituted aryl" refers to aryl groups bearing one or more substituents.

The term "arylalkynyl" refers to aryl-substituted alkynyl groups and "substituted arylalkynyl" refers to arylalkynyl groups further bearing one or more substituents.

The term "aroyl" refers to aryl-substituted species such as benzoyl and "substituted aroyl" refers to aroyl moieties further bearing one or more substituents as set forth above.

The term "cycloalkyl" refers to cyclic ring-containing moieties containing in the range of about 3 up to 7 carbon atoms and "substituted cycloalkyl" refers to cycloalkyl moieties further bearing one or more substituents.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and having in the range of 2 up to 12 carbon atoms, or preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbamate, carbocyclo, carboxyl, cyano, ester, ether, halogen, heteroaryl, heterocyclo, hydroxyl, keto, ketal, phospho, nitro, thio, trifluoromethyl, sulfonyl, sulfonamide, and the like.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
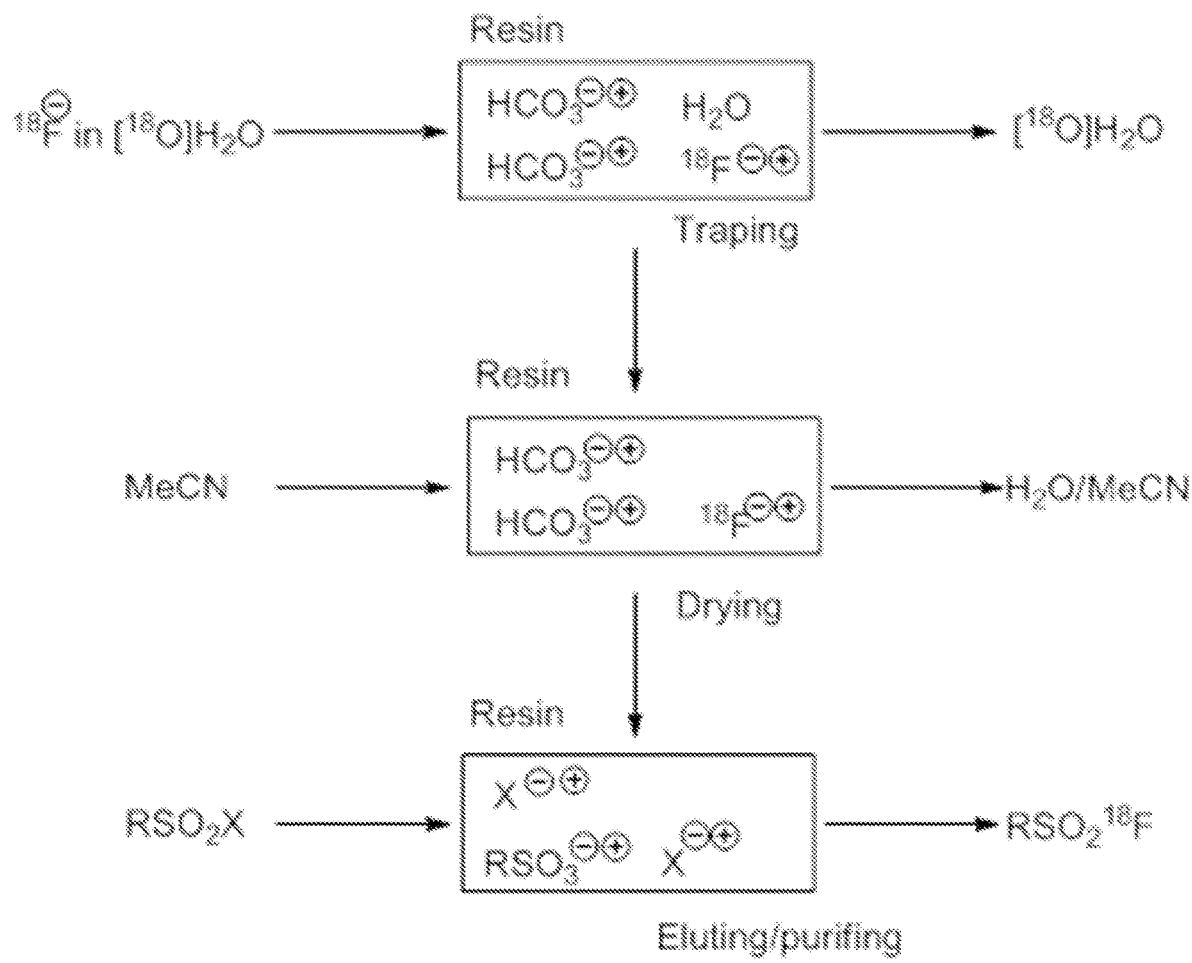
FIG. 2 depicts a schematic showing the process of trapping, drying, eluting and purifying in an anion exchange resin.

Formation of [$^{18}$F]Sulfonyl Fluoride in Aqueous Solution and Downstream Uses Sulfonyl fluoride can be formed quantitatively from the reaction of fluoride with sulfonyl chloride or other sulfonates even in aqueous solution (Table 1). Due to the electronegativity of fluorine, fluoride is formed exclusively from the sulfonyl-fluorine bond cleavage by a base or a nucleophile. This provides the basis for using [F-18]sulfonyl fluoride as the source of [F-18]fluoride for nucleophilic radiolabeling of F-18 radiopharmaceuticals. The S—F bond in sulfonyl fluoride is much more stable than the S—Cl bond in sulfonyl chloride. Under a basic condition in an anion exchange resin, sulfonyl chloride will decompose to form sulfonate and chloride, which will be trapped by the resin; while formed sulfonyl fluoride will be eluted as a neutral compound under these conditions. Therefore, the use of anion exchange resin provides a method to generate and purify [F-18]sulfonyl fluoride for radiolabeling of F-18 radiopharmaceuticals (FIG. 2). This method can also be used to generate [F-18]acyl fluorides and [F-18]silyl fluorides for radiolabeling. F-18 labeling is typically carried out through a nucleophilic substitution of a good leaving group (e.g. TsO, MsO, TfO) by [F-18]fluoride in the presence of $K_2CO_3/K_{222}$, one function of which is to convert any formed sulfonyl fluoride back to fluoride for the completion of radiolabeling. Under some conditions, [F-18]tosyl fluoride has been observed as a radioactive by-product.

TABLE 1

Formation of [$^{18}$F] sulfonyl fluoride in aqueous solution.

| R | Yield (%)[1] | | | | |
|---|---|---|---|---|---|
| | 5 min | 10 min | 15 min | 30 min | 60 min |
| 4-MeO | 7.7 | 14.7 | 18.6 | 30.9 | 46.2 |
| 2-Me | 16 | 36.1 | 53.14 | 70.6 | 85.9 |
| 3-Me | 13 | 27.6 | 50.2 | 59 | 81.2 |

TABLE 1-continued

Formation of [$^{18}$F] sulfonyl fluoride in aqueous solution.

$$\text{R-C}_6\text{H}_4\text{-SO}_2\text{-Cl} + {}^{18}\text{F}^- \xrightarrow[\text{RT}]{\text{1:1 MeCN/PBS}} \text{R-C}_6\text{H}_4\text{-SO}_2\text{-}{}^{18}\text{F}$$

| R | Yield (%)[1] | | | | |
|---|---|---|---|---|---|
| | 5 min | 10 min | 15 min | 30 min | 60 min |
| 4-Me | 10.6 | 19 | 27.4 | 50.3 | 75.3 |
| 2-F | 24.8 | 37.5 | 53.9 | 81.3 | 93.6 |
| 3-F | 39.4 | 57.8 | 78.2 | 94.8 | 100 |
| 4-F | 17.2 | 35.3 | 48.2 | 77.7 | 90.7 |
| 2-Cl | 24.4 | 43.5 | 77.1 | 91 | 98.7 |
| 3-Cl | 37.9 | 69 | 70.5 | 98.9 | 100 |
| 4-Cl | 41.9 | 69.8 | 82.3 | 95.1 | 98.1 |
| 4-Br | 34.3 | 56.5 | 83.6 | 95.2 | 99.5 |
| 4-I | 27.8 | 57.6 | 82.2 | 95.7 | 99.7 |
| 2-CF$_3$ | 57.5 | 71.1 | 92.2 | 100 | 100 |
| 3-CF$_3$ | 53.8 | 79.2 | 90.3 | 100 | 100 |
| 4-CF$_3$ | 70.8 | 91 | 96 | 100 | 100 |
| CH$_3$CO | 79.5 | 96.8 | 99.3 | 100 | 100 |
| 2-CN | 90.6 | 97.1 | 98 | 100 | 100 |
| 4-CN | 92.4 | 97.4 | 98 | 98.5 | 98.1 |
| 2-Py | 99.2 | 99.3 | 99.1 | 98.9 | 98.3 |
| 4-NO$_2$ | 96.7 | 97 | 96.5 | 97.3 | 98.3 |

[1]Determined by radio TLC and confirmed by radio HPLC.

Figure 3:
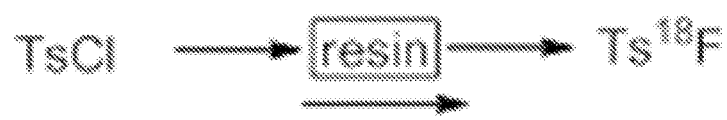
FIG. 3 depicts a schematic showing the methods of elution/purification.
Figure 3:
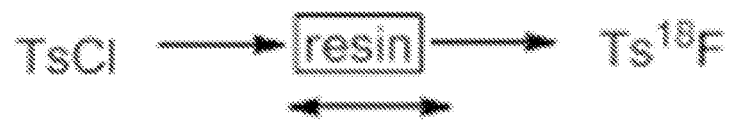
Figure 3:
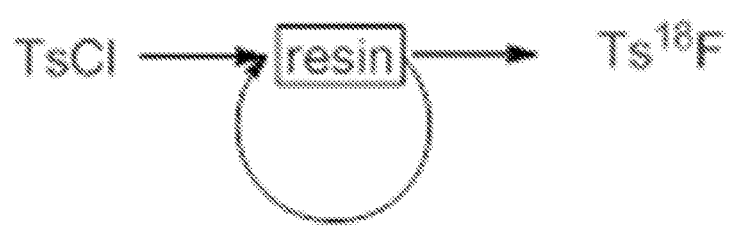

Sulfonyl chloride in the eluting solution has several functions. It can react directly with [F-18]fluoride on the anion exchange resin to form [F-18]sulfonyl fluoride and chloride. [F-18]Sulfonyl fluoride will be eluted from the resin as a neutral compound while chloride will be trapped by the resin. Due to the instability of sulfonyl chloride towards the basic condition of anion exchange resin, sulfonyl chloride will be decomposed by the resin to form sulfonyl acid and hydrogen chloride, which are then neutralized by bicarbonate or carbonate in the resin to form sulfonate and chloride. Both of them will be trapped by the anion exchange resin. The formed acids or salts from the decomposition of sulfonyl chloride can also release trapped [F-18]fluoride from the resin and facilitate the formation of sulfonyl fluoride. Therefore, the addition of sulfonyl acid (e.g. TsOH) to the eluting solution is beneficial to this method. Due to this eluting mechanism, only neutral compounds will be eluted from the resin. Sulfonyl chloride may co-elute with [F-18]sulfonyl fluoride, but this amount of sulfonyl chloride is tolerated by the labeling reaction because sulfonyl chloride will be decomposed instantly by the basic labeling condition and the formed sulfonate and chloride will not be able to compete with fluoride in the labeling. The eluting efficiency of F-18 as sulfonyl fluoride is determined by the resin, substrate (e.g. sulfonyl chloride or sulfonyl anhydride), the addition of co-eluent, temperature, contact time (length of resin and flow rate). One elution can result up to 95% conversion of fluoride and remove up to 99% sulfonyl chloride. Reloading the eluted solution to the same resin or a second resin will completely remove sulfonyl chloride with 97% conversion of fluoride under optimized conditions (FIG. 3).

The formed [F-18]sulfonyl fluoride has high UV absorbance, which allows it to be detected by HPLC conveniently for QC purpose or determining the specific activity of fluoride; it is stable in neutral solution, allowing it to be stored for a day and used for synthesis-on-demand; the low volume of sulfonyl fluoride solution and flexible amount of other reagents for labeling is ideal for new technologies.

Example 2

Elution of [$^{18}$F]Tosyl Fluoride in Different Solvents

[F-18]fluoride in water (1 mL) was loaded onto a 30-PS-HCO$_3$ cartridge, and the cartridge was rinsed with the specified solvent (5 mL) at room temperature or 80° C. The cartridge was eluted by a solution of tosyl chloride (1 mg) in the specified solvent (0.5 mL), and followed by rinsing with the specified solvent (0.5 mL). The cartridge and the elution were measured by a dose calibrator to determine the elution efficiency (%). The results are shown in Table 2.

TABLE 2

Elution of [$^{18}$F]tosyl fluoride in different solvents

| Solvent | TsCl (mg) | Temp | TsF (%) |
|---|---|---|---|
| MeCN | 1/0.5 mL + 0.5 mL | 80° C. | 95 |
| MeCN | 1/0.5 mL + 0.5 mL | RT | 95 |
| amyl alcohol | 1/0.5 mL + 0.5 mL | 80° C. | 98 |
| THF | 1/0.5 mL + 0.5 mL | RT | 92.5 |
| 1,2-dichlorobenzene | 1/0.5 mL + 0.5 mL | RT | 36 |
| EtOH | 1/0.5 mL + 0.5 mL | RT | 96.7 |
| DMF | 1/0.5 mL + 0.5 mL | RT | 77 |
| DMF | 1/0.5 mL + 0.5 mL | 80° C. | 93.6 |

Example 3

Elution of [$^{18}$F]TsF Using Different Anion Exchange Resin

[F-18]fluoride in water (1 mL) was loaded onto the specified resin in a cartridge, and the resin was rinsed with acetonitrile (5 mL). The resin was eluted by a solution of tosyl chloride (1 mg) in acetonitrile (0.5 mL), and followed by rinsing with acetonitrile (0.5 mL). The resin and the elution were measured by a dose calibrator to determine the elution efficiency (%). The results are shown in Table 3.

TABLE 3

Elution of [$^{18}$F]TsF using different anion exchange resin.

| Resin | Ts$^{18}$F (%) |
|---|---|
| MACHEREY-NAGEL 30-PS-HCO$_3$ | 95-97 |
| Bio-Rad MP-1M | 90-95 |
| Bio-Rad Bio-Rex 5 | 91-94 |
| MACHEREY-NAGEL Chromafix PS-OH | 91 |
| Phenomenex Strata-X-A | 90-95 |
| Waters QMA | 49 |
| Waters MAX | 93 |

Example 4

Elution of [$^{18}$F]TsF Using Different Eluting Agents

[F-18]fluoride in water (1 mL) was loaded onto a 30-PS-HCO$_3$ cartridge, and the cartridge was rinsed with acetonitrile (5 mL). The resin was eluted by a solution of the specified eluting agent (1 mg) in acetonitrile (0.5 mL), and followed by rinsing with acetonitrile (0.5 mL). The resin and the elution were measured by a dose calibrator to determine the elution efficiency (%). The results are shown in Table 4.

TABLE 4

Elution of $^{18}$F sulfonyl fluoride with different eluting agents

| R | X | RSO$_2$F (%) |
|---|---|---|
| 4-NO$_2$ | Cl | 70-90 |
| 2-CN | Cl | 60-80 |
| 4-Me | OTf | 93-97 |
| 4-Me | OTs | 92 |
| 2-Cl | Cl | 79 |
| 4-MeO | Cl | 93 |
| 2,4,6-trimethylbenzene | Cl | 95.3 |
| 4-CF3 | Cl | 86 |
| 2-Pyridinesulfonyl chloride | | 80 |
| PhN(OTf)$_2$ | | 56 |
| MsOMs | | 58 |

Example 5

Elution of [$^{18}$F]TsF

1. [$^{18}$F]fluoride (22.6 mCi)[1] in water (1 mL) was loaded onto a 30-PS-HCO3 cartridge;
2. Rinse the cartridge with acetonitrile (1 mL) at room temperature;
3. Rinse the cartridge with acetonitrile (4 mL) heated at 80° C.;
4. Elute the cartridge with TsCl (1 mg) in acetonitrile (0.5 mL) heated at 80° C. and rinse with acetonitrile (0.5 mL);
5. [$^{18}$F]TsF (18.9 mCi) is collected in acetonitrile (1 mL).

Results:
Conversion efficiency: 95.8%
Radiochemical purity: >99.9%
Specificity activity: 43000 mCi/µmol (decay corrected to EOB)
Note: [1] 141 mCi at the end of bombardment (EOB).

Example 6

Elution of [$^{18}$F]TsF in Portions

1. [$^{18}$F]fluoride (6 mCi) in water (1 mL) containing 0.58 ppm potassium fluoride[1] was loaded onto a 30-PS-HCO3 cartridge;
2. Rinse the cartridge with acetonitrile (5 mL) at room temperature;
3. Elute the cartridge with a solution of TsCl in acetonitrile (0.2 mg in 1 mL) at room temperature in a portion of 1 mL.

Results:
Elution-1: 76.7%
Elution-2: 16%
Elution-3: 3.6%
Elution-4: 1.2%
Left in 30-PS-HCO$_3$: 2.6%
Note: [1] Potassium fluoride is added to simulate mass in large amount of radioactivity.

Example 7

Generation of [$^{18}$F]TsF Via Circulating TsCl

[$^{18}$F]fluoride (5 mCi) in water (1 mL) was loaded onto a cartridge containing MP-1 M-HCO$_3$ resin (30 mg). The resin was rinsed with acetonitrile (5 mL) at room temperature. A solution of TsCl (1 mg) and TsOH.H$_2$O (0.25 mg) in acetonitrile (0.5 mL) was circulating the resin at 3 mL/min for 3 min at room temperature, and then the resin was rinsed with acetonitrile (0.5 mL) and [$^{18}$F]TsF was collected in acetonitrile (1 mL) in 95% yield.

Example 8

Synthesis of F-18 Labeled Compounds

Synthesis of FDG.

Into a reaction vessel containing potassium carbonate/K222 (1:2 5 mg) was added [$^{18}$F]TsF in acetonitrile (300 4), which was from a elution of a 30-PS-HCO3 cartridge with TsCl. The mixture was heated at 105° C. for 2 min, and then at 80° C., a solution of FDG precursor (5 mg) in acetonitrile (200 µL) was added. The reaction mixture was heat at 80° C. for 7 min to complete the labeling. Radio-TLC and radio-HPLC showed 98% yield as the FDG intermediate and total consummation of [$^{18}$F]TsF in the reaction mixture.

Synthesis of FMISO.

Into a reaction vessel containing potassium carbonate/K222 (1:2 2.5 mg) and NITTP (FMISO precursor) (2 mg) was loaded [$^{18}$F]TsF in acetonitrile (500 4), which was from circulating TsCL (1 mg), TsOH.H$_2$O (0.25 mg) in acetonitrile (0.5 mL). The mixture was heated at 102° C. for 10 min to complete the labeling. Radio-TLC and radio-HPLC showed 95% yield as the FMISO intermediate and total consummation of [$^{18}$F]TsF in the reaction mixture.

A summary of radiolabeling is shown in Table 5.

TABLE 5

Exemplary Synthesized Compounds.

| Name[1] | RCC (%)[3] | Leaving group | Amount (mg) | Reaction condition |
|---|---|---|---|---|
| FDG[2] | 98 | OTf | 5 | 80° C. 8 min |
| FLT[2] | 60-80 | ONs | 2 | 80-105° C. 7-10 min |
| FMISO[2] | 95 | OTs | 2 | 102° C. 10 min |
| Fallypride | 91 | OTs | 1 | 105° C. 7 min |
| FES | 80 | Cyclic SO$_2$ | 0.3 | 105° C. 7 min |
| FFNP | 70 | OMs | 2 | 65° C. 7 min |
| FNOS | 74 | OMs | 4.1 | 100° C. 7 min |
| 2-Fluoroethyltosylate | 97 | OTs | 2.8 | 105° C. 7 min |
| 2-Fluoroethylazide | 95 | OTs | 2.2 | 80° C. 8 min |
| WC-4-138 | 95 | OTs | 1.3 | 105° C. 10 min |
| WC-4-138 | 83 | Br | 1.8 | 105° C. 10 min |

TABLE 5-continued

Exemplary Synthesized Compounds.

| Name[1] | RCC (%)[3] | Leaving group | Amount (mg) | Reaction condition |
|---|---|---|---|---|
| FC$_9$COOMe | 97 | Br | 2.9 | 105° C. 10 min |
| 4-Fluorobenzaldehyde | 94 | $^+$NMe$_3$I | 3.2 | 105° C. 8 min |
| 4-Fluorobenzoate ethyl | 93 | $^+$NMe$_3$OTs | 2.8 | 105° C. 10 min |

Note
[1]FDG, FLT, Fallypride, FES, FFNP, FNOS, WC-4-138 are clinical PET tracers;
[2]as intermediate;
[3]Radiochemical yield, determined by radioTLC.

What is claimed is:

1. A method of making [F-18]sulfonyl fluoride suitable as a source of [F-18] fluoride for use in a labeling reaction without further purification, wherein the method does not comprise an evaporation step, and wherein the method comprises:
   a) passing an aqueous [F-18]fluoride solution or solvent through a solid phase extraction column comprising an anion-exchange resin so that the [F-18]fluoride is trapped on the resin;
   b) rinsing the resin with an organic solvent to eliminate the residual water; and
   c) eluting the [F-18]fluoride with an eluting solution to release the [F-18]fluoride from the anion-exchange resin as [F-18]RSO$_2$F which acts as a source of [F-18] fluoride for the labeling reaction, wherein the eluting solution comprises a compound having the formula RSO$_2$R$^1$, a co-eluting agent, and an organic solvent, wherein
   R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, and combinations thereof; and
   R$^1$ is a leaving group.

2. The method of claim 1, wherein R is selected from the group consisting of alkyl, substituted alkyl, cycloalkyl, substituted cycloalkyl, aryl, substituted aryl, heteroaryl, substituted heteroaryl, methyl and trifluoromethyl.

3. The method of claim 1, wherein R is selected from the group consisting of CH$_3$, CF$_3$, C$_6$H$_5$, CH$_3$C$_6$H$_4$, CF$_3$C$_6$H$_4$, NO$_2$C$_6$H$_4$, ClC$_6$H$_4$, FC$_6$H$_4$, BrC$_6$H$_4$, IC$_6$H$_4$, CH$_3$COC$_6$H$_4$, MeOC$_6$H$_4$, CNC$_6$H$_4$, Me$_2$NC$_6$H$_4$, 2,4,6-(CH$_3$)$_3$C$_6$H$_2$, and C$_5$H$_5$N (pyridine).

4. The method of claim 1, wherein R$^1$ is selected from the group consisting of Cl$^-$, Br$^-$, I$^-$, tosylate (TsO), mesylate (MsO), and trifluoromethanesulfate (triflate; TfO).

5. The method of claim 1, wherein RSO$_2$ is selected from the group consisting of tosyl (Ts), mesyl (Ms), trifluoromethanesulfonyl (Tf), nosyl (Ns), besyl (Bs), and N-phenyl-trifluoromethanesulfonimide (NTfPh).

6. The method of claim 1, wherein RSO$_2$R$^1$ is selected from the group consisting of tosyl chloride, mesyl chloride, trifluoromethanesulfonyl chloride, nosyl chloride, N-Phenyl-bis(trifluoromethanesulfonimide), tosyl anhydride, mesyl anhydride, trifluoromethanesulfonic anhydride, tosyl mesylate, and tosyl triflate.

7. The method of claim 1, wherein the organic solvent is selected from the group consisting of acetonitrile, dimethylformamide, 2-amyl alcohol, tetrahydrofuran, and ethanol.

8. The method of claim 1, wherein the eluting co-eluting agent is selected from the group consisting of TsOH/TsO$^-$, MsOH/MsO$^-$, TfOH/TfO$^-$, HCl/Cl$^-$, H$_2$SO$_4^-$/HSO$_4^-$/SO$_4^{2-}$, AcOH/AcO$^-$ and TsOH.H$_2$O.

9. The method of claim 1, wherein the anion exchange resin comprises a polymeric matrix and quaternary ammonium groups.

10. The method of claim 1, wherein the eluting is done via a back-and-forth method or a circulating method.

11. The method of claim 1, further comprising regenerating the [F-18]fluoride in the presence of at least one base and at least one phase transfer catalyst during or before a labeling reaction.

12. The method of claim 11, wherein the base is selected from the group consisting of potassium carbonate (K$_2$CO$_3$), potassium bicarbonate (KHCO$_3$), cesium carbonate (Cs$_2$CO$_3$), cesium biocarbonate, and tetrabutylammonium and tetramethylammonium salts (hydroxide, carbonate, and bicarbonate).

13. The method of claim 11, wherein the base and phase transfer catalyst are pre-dried prior to use.

14. The method of claim 11, wherein regeneration is carried out under anhydrous or aqueous conditions.

15. The method of claim 1, wherein the [F-18]sulfonyl fluoride is used to measure concentration and specific activity of fluoride.

16. The method of claim 1, wherein the eluted solution containing the [F-18]sulfonyl fluoride is used for the synthesis of a PET radiotracer.

17. The method of claim 16, wherein (a) the [F-18] fluoride is regenerated prior to synthesis of the PET radiotracer by mixing (i) at least one base with or without at least one phase transfer catalyst and (ii) the [F-18]sulfonyl fluoride, and heating the mixture; or (b) the [F-18]fluoride is regenerated during synthesis of the PET radiotracer by mixing (i) at least one base with or without at least one phase transfer catalyst, (ii) the [F-18]sulfonyl fluoride, and (iii) an aliphatic or aromatic precursor, and heating the reaction mixture.

18. The method of claim 16, wherein the PET radiotracer is selected from the group consisting of FDG, FLT, fallypride, FES, FFNP, FNOS, fluoroethyltosylate, fluoroethylazide, FC$_9$COOMe, 4-fluorobenzaldehyde and 4-fluorobenzoate ethyl ester.

\* \* \* \* \*